US009237946B2

(12) United States Patent
Pynson (10) Patent No.: US 9,237,946 B2
(45) Date of Patent: Jan. 19, 2016

(54) THIN IOL (75) Inventor: Joel Pynson, Toulouse (FR)

(73) Assignee: Bausch & Lomb Incorporated, Rochester, NY (US)

( * ) Notice: Subject to any disclaimer, the term of this patent is extended or adjusted under 35 U.S.C. 154(b) by 2117 days.

(21) Appl. No.: 11/719,471

(22) PCT Filed: Nov. 18, 2005

(86) PCT No.: PCT/IB2005/003676
§ 371 (c)(1),
(2), (4) Date: Mar. 18, 2009

(87) PCT Pub. No.: WO2006/054178
PCT Pub. Date: May 26, 2006

(65) Prior Publication Data
US 2009/0228102 A1 Sep. 10, 2009

(30) Foreign Application Priority Data

Nov. 19, 2004 (WO) .................. PCT/IB2004/004106

(51) Int. Cl.
A61F 2/16 (2006.01)
(52) U.S. Cl.
CPC ................ A61F 2/1616 (2013.01); A61F 2/16 (2013.01); A61F 2/1648 (2013.01); A61F 2002/1681 (2013.01)
(58) Field of Classification Search
CPC ....... A61F 2/16; A61F 2/1648; A61F 2/1616; A61F 2002/1681–2002/1689; A61F 2002/1697
USPC ............... 623/6.11, 6.38, 6.43–6.47
See application file for complete search history.

(56) References Cited

U.S. PATENT DOCUMENTS

| 4,087,866 A | 5/1978 | Choyce et al. |
| 4,134,161 A | 1/1979 | Bayers |
| 4,261,065 A | 4/1981 | Tennant |
| 4,872,876 A | 10/1989 | Smith |
| 5,326,506 A | 7/1994 | Vanderbilt |
| 5,476,513 A | 12/1995 | Brady et al. |
| 5,609,630 A | 3/1997 | Crozafon |
| 5,674,282 A | 10/1997 | Cumming |
| 5,928,282 A | 7/1999 | Nigam |
| 5,944,725 A | 8/1999 | Cicenas et al. |
| 6,051,024 A | 4/2000 | Cumming |
| 6,162,249 A * | 12/2000 | Deacon et al. ............... 623/6.16 |
| 6,200,344 B1 | 3/2001 | Lamielle et al. |
| 6,224,628 B1 | 5/2001 | Callahan |

(Continued)

FOREIGN PATENT DOCUMENTS

GB 1 547 200 6/1979
JP H8-076067 3/1996

(Continued)

OTHER PUBLICATIONS

International Search Report (PCTISA/210) and Written Opinion (PCT/ISA/237) mailed on Aug. 11, 2006.

(Continued)

Primary Examiner — Howie Matthews
(74) Attorney, Agent, or Firm — Toan P. Vo (57) ABSTRACT A thin IOL capable of insertion through a small incision into the capsular bag of an eye includes haptics having free ends configured to absorb compressive forces resulting from shrinkage of the capsular bag in the weeks following surgery.

29 Claims, 8 Drawing Sheets

(56) References Cited

U.S. PATENT DOCUMENTS

| | | |
|---|---|---|
| 6,228,115 B1 | 5/2001 | Hoffmann et al. |
| 6,322,589 B1 | 11/2001 | Cumming |
| 6,336,932 B1 | 1/2002 | Figueroa et al. |
| 6,406,494 B1 | 6/2002 | Laguette et al. |
| 6,425,917 B1 | 7/2002 | Blake |
| 6,749,634 B2 | 6/2004 | Hanna |
| 6,827,738 B2 | 12/2004 | Willis et al. |
| 6,849,091 B1 | 2/2005 | Cumming |
| 6,926,744 B1 | 8/2005 | Bos et al. |
| 2001/0016771 A1 | 8/2001 | Cumming |
| 2002/0035398 A1 | 3/2002 | Cumming |
| 2002/0103536 A1 | 8/2002 | Landreville et al. |
| 2002/0193877 A1 | 12/2002 | Hoffmann et al. |
| 2003/0014107 A1 | 1/2003 | Reynard |
| 2003/0097177 A1 | 5/2003 | Tran |
| 2003/0187505 A1 | 10/2003 | Liao |
| 2003/0199977 A1 | 10/2003 | Cumming |
| 2003/0204257 A1 | 10/2003 | Southard |
| 2004/0215340 A1 | 10/2004 | Messner et al. |
| 2005/0015143 A1 | 1/2005 | Willis et al. |
| 2005/0021140 A1 | 1/2005 | Liao |
| 2005/0107875 A1 | 5/2005 | Cumming |
| 2005/0119741 A1 | 6/2005 | Cumming |
| 2005/0187621 A1 | 8/2005 | Brady |
| 2005/0246017 A1 | 11/2005 | Messner et al. |
| 2006/0020339 A1 | 1/2006 | Ran |

FOREIGN PATENT DOCUMENTS

| | | |
|---|---|---|
| JP | P2003-25203 A | 1/2003 |
| WO | WO 97/12564 A1 | 4/1997 |
| WO | WO 01/15635 | 3/2001 |
| WO | WO 03/077803 A1 | 9/2003 |
| WO | WO 03/082147 | 10/2003 |
| WO | WO 03/082147 A2 | 10/2003 |
| WO | WO 03/092553 | 11/2003 |
| WO | 2004030580 A1 | 4/2004 |
| WO | WO 2005/016190 | 2/2005 |
| WO | WO 2005/032427 A1 | 4/2005 |

OTHER PUBLICATIONS

Corresponding Japanese Office Action dated Jun. 25, 2013.

* cited by examiner

THIN IOL

BACKGROUND OF THE INVENTION

The present invention relays to intraocular lenses (also commonly referred to as IOLs), and more particularly relates to a thin IOLs that can be inserted through a very small incision in the eye and into the evacuated capsular bag of an eye.

Cataract surgery commonly involves removal of the eye's natural but clouded lens which is located in the capsular bag using a surgical technique known as phacoemulsification. It is desirable to have an incision in the eye as small as possible to improve heating and discourage formation of post-cataract astigmatism caused by the healed incision. The standard of today's incision size is 3 mm or less. With even more recent surgical techniques, i.e. bi-manual phacoemulsification or laser-phaco, incisions of less than 2 mm are possible. Of course if the IOL and/or the insertion instrument are larger than the incision size, the incision must be enlarged.

In order to pass a flexible IOL through a small incision, it must be compressed to a smaller size and inserted in the eye using an instrument such as forceps or an IOL inserter. Examples of IOL inserters may be seen in commonly assigned U.S. Pat. Nos. 5,944,725 and 6,336,932. It will thus be appreciated that the material and dimensions of the IOL will dictate how small the IOL may be compressed without undergoing damage (i.e., larger dimensioned IOLs will not compress as small as a smaller sized IOL). Of course, the IOL cannot be so small as to lose its intended purpose of restoring the function of the eye's natural lens. Proper functioning of the IOL requires the IOL to remain as stable as possible in the eye since movement thereof can distort the light rays passing therethrough onto the retina Positioning elements known as haptics are thus incorporated into the IOL design to help position and stabilize the optic in the capsular bag Many different haptic configurations exist yet there remains a need for an IOL of a relatively small size which allows the lens to be compressed and delivered through a small incision, preferably on the order of about 2 mm or less, while also maintaining the optic very stably in the eye despite compressive forces being applied thereto. Compressive forces may occur, for example, from shrinkage of the capsular bag which occurs in the few months following cataract extraction surgery.

SUMMARY OF THE INVENTION

Aspects of the present invention address the above stated need by providing a in, foldable, IOL for placement in an evacuated capsular bag of an eye, the IOL comprising an optic having opposite anterior and posterior surfaces surrounded by a periphery. In an embodiment, four flexible haptics extend radially outwardly from the periphery, the haptics each having an elongated section and terminating in a free end. The first and second haptics are spaced from one another along a first portion of the optic edge and the third and fourth haptics are spaced from one another along a second portion of the optic edge which is opposite the first portion of the optic edge.

In some embodiments, the bee end of each haptic include at least two spaced fingers that extend in an anterior direction. The fingers flex and decrease the radius of curvature thereof in response to a radial compressive force applied thereto while the optic remains substantially aligned along the eye's optical axis. The fingers may also move toward one another to absorb the tangential forces imparted by the shrinking capsular bag. In some embodiments, the fingers each have a length preferably about a quarter the length of the respective elongated sections. In a further preferred embodiment of the invention, the proximal haptic length is thicker than respective distal haptic length.

In a preferred embodiment, the IOL further comprises a sharp edge defined along the optic periphery. When inserted into the evacuated capsular bag of an eye, the sharp edge presses against the posterior wall of the bag and acts as a barrier against cellular migration and posterior capsular opacification caused thereby.

Embodiments of the invention are direct to a foldable IOL, comprising: a) an optic having a geometric center and a periphery, b) at least two haptics coupled to said optic, each having a proximal end and a distal end, each of said haptics having a thickness that decreases by at least 10% from the proximal end to the distal end. In some of the embodiments, each of said haptics has a thickness that decreases from the proximal end to the distal end by 10% to 60%. In some of the embodiments, each of said haptics has a thickness that decreases from the proximal end to the distal end by 15% to 40%. In some embodiments, the decrease in thickness in each haptic is measured over a central 65% portion of each haptic. Each haptic may include at least one step. In some embodiments, each haptic includes at least two steps. In some embodiments, the thickness decreases smoothly over the length of the haptics. In some embodiments, the thickness decreases linearly over the length of the haptics. The thickness may decrease monotonically over the length of the haptics.

Some embodiments are directed to a foldable IOL, comprising a) an optic having a geometric center and a periphery, b) at least two flexible haptics coupled to the optic, each haptic having an anterior surface and a posterior surface, and a proximal end and a distal end, each haptic being concave on the anterior surface between the proximal end and distal end. In some embodiments, at least one of the haptics has a single curvature between the proximal end and the distal end. In some embodiments, at least one of the haptics has at least two curvatures between the proximal end and the distal end. In some embodiments, at least one of the haptics has a curvature that varies continuously between the proximal end and the distal end. In some embodiments, for at least one of the haptics, the curvature of the anterior surface and the posterior surface is substantially the same.

Dimensions and measurements as described herein refer to a finished (i.e., hydrated) lens. The dimensions are measured while supporting the IOL using the posterior surface of the optic.

DETAILED DESCRIPTION OF PREFERRED EMBODIMENT

Figure 1:
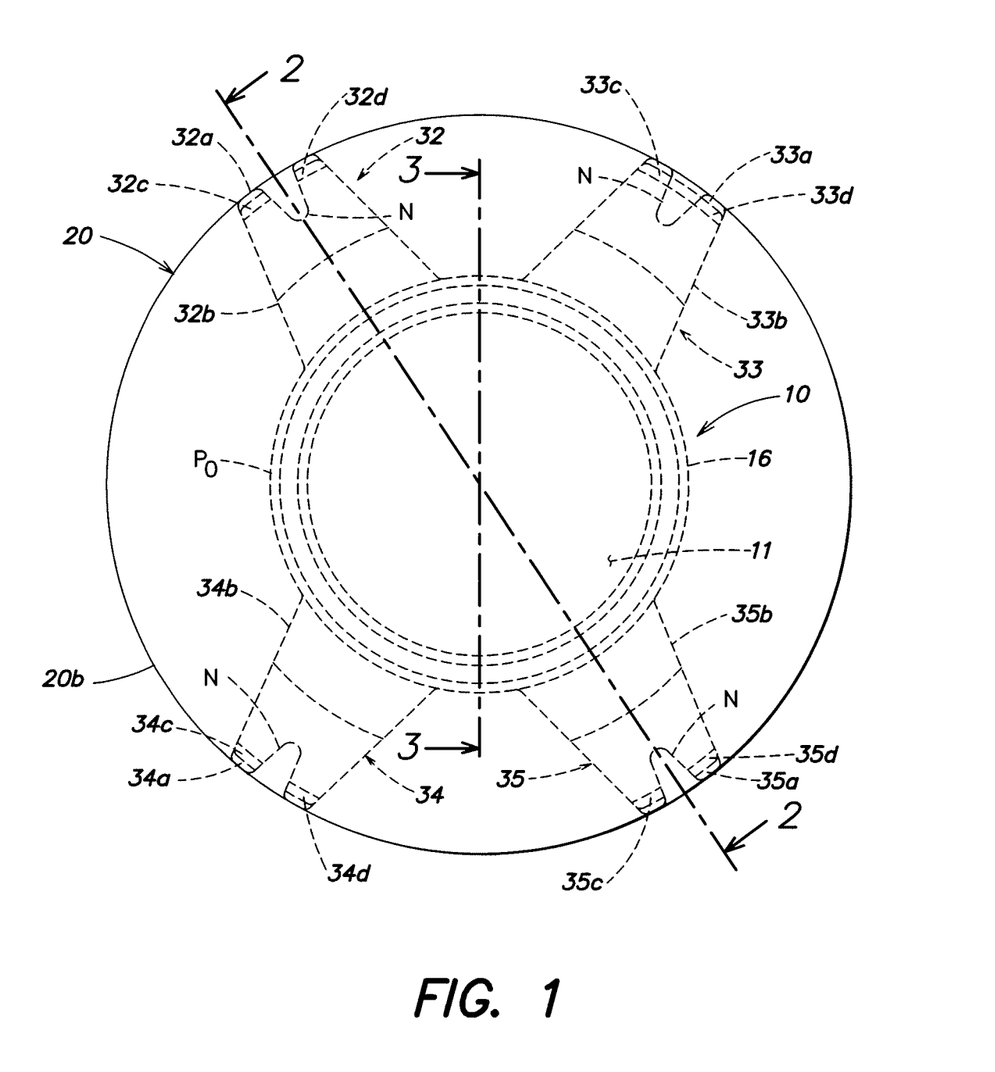
FIG. 1 is a plan view of an IOL according to an embodiment of the invention as implanted in a capsular bag.
Figure 2:
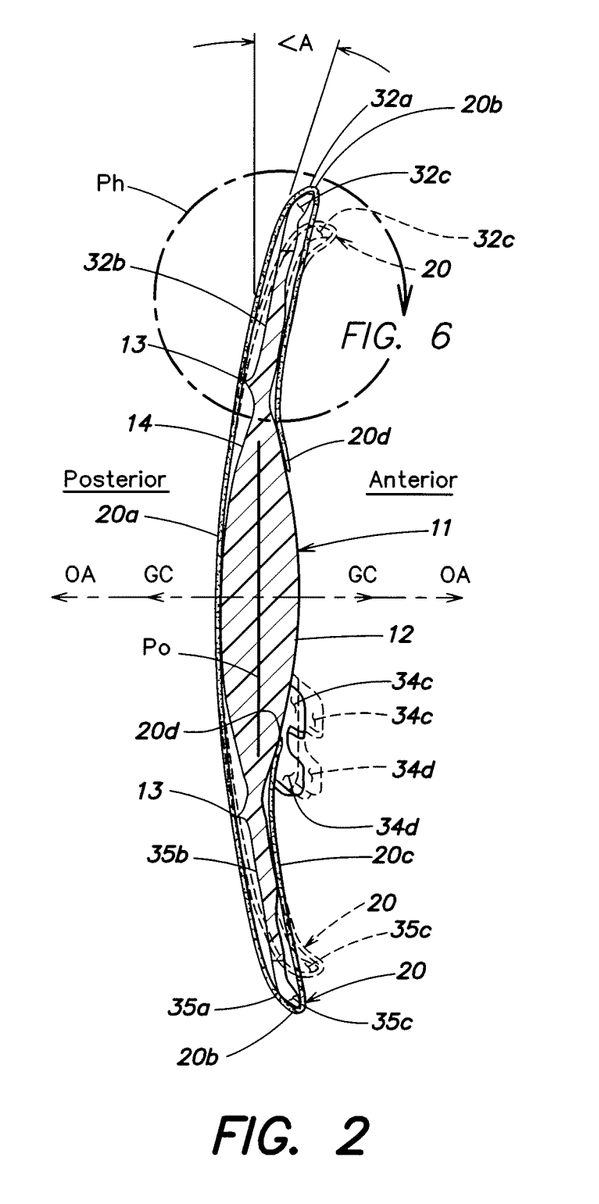
FIG. 2 is a cross-sectional view thereof as taken generally along the line 2-2 of FIG. 1.
Figure 3:
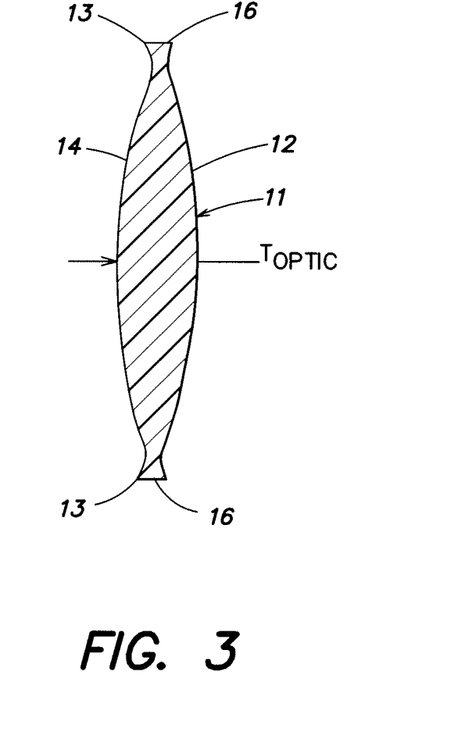
FIG. 3 is a cross-sectional view thereof as taken along the line 3-3 of FIG. 1.

Referring now to the drawings, there is seen in the various Figures a preferred embodiment of an IOL (IOL) 10 according to the invention. IOL 10 includes an optic 11 having opposite anterior and posterior surfaces 12, 14, respectively, defining a geometric center GC and a periphery 16. The terms "anterior" and "posterior" refer to the anterior and posterior directions when IOL 10 is implanted in an eye. The anterior direction from the vantage point of the eye's capsular bag is toward the cornea. The posterior direction is toward the retina. The capsular bag 20 is schematically represented in FIGS. 1 and 2. When implanted in the eye in the intended manner, IOL anterior surface 12 would thus face the cornea while the posterior surface 14 would Ace the retina.

Optic 11 is configured to direct light rays onto the eye's retina and thus replace the function of the eye's natural lens following removal thereof during cataract surgery. Optic 11 can be of any desired foldable material such as acrylic and silicone, for example, and the anterior and posterior surfaces 12, 14 may be of any desired optical design and combination thereof including planar, convex, concave, spherical and aspherical (including toric and multifocal). In the embodiment shown in the Figures, optic 11 is biconvex merely for purposes of discussion. In this embodiment, the optic preferably has a maximum thickness $T_{optic}$ of between about 0.7 to 0.9 mm.

The IOL of the invention is intended for surgical implantation into the eye's capsular bag 20. The eye's natural lens is encased in a structure known as the capsular bag. The surgeon makes an opening (called a capsulorhexis) in the anterior wall 20c of the capsular bag 20 leaving an anterior wall flap 20d (see FIG. 2). The capsulorhexis is sized to be about 1 mm less than the diameter of the IOL optic such that the anterior wall flap rests against the anterior surface of the IOL optic 11.

As described previously, the capsular bag 20 will shrink for about 3 months following surgery and this creates compressive forces on the implanted IOL. It is preferred that the IOL 10 be implanted such that the geometric center axis GC of optic 11 is substantially aligned along the eye's optical axis OA (FIG. 2) and that this alignment be maintained in the presence of compressive forces being applied to the IOL. The present invention therefore provides an IOL designed to absorb these compressive forces while maintaining the optic geometric center GC substantially aligned along the optical axis OA. This is a particularly challenging endeavor when designing an IOL of thin construction.

According to one aspect of the invention, one or more haptics 30 extend from the optic periphery 16, the haptics being formed of a flexible material and configured to absorb compressive forces applied thereto. In a preferred embodiment, the haptics extend anteriorly at an angle "A" of about 5 to 15 degrees relative to the plane of the optic 11 (this angle is typically referred to as the vault angle). The terms "anterior", "anteriorly" and "anterior direction" are meant to refer to the anterior direction (toward the cornea) when IOL 10 is implanted in an eye as described above.

Figure 6:
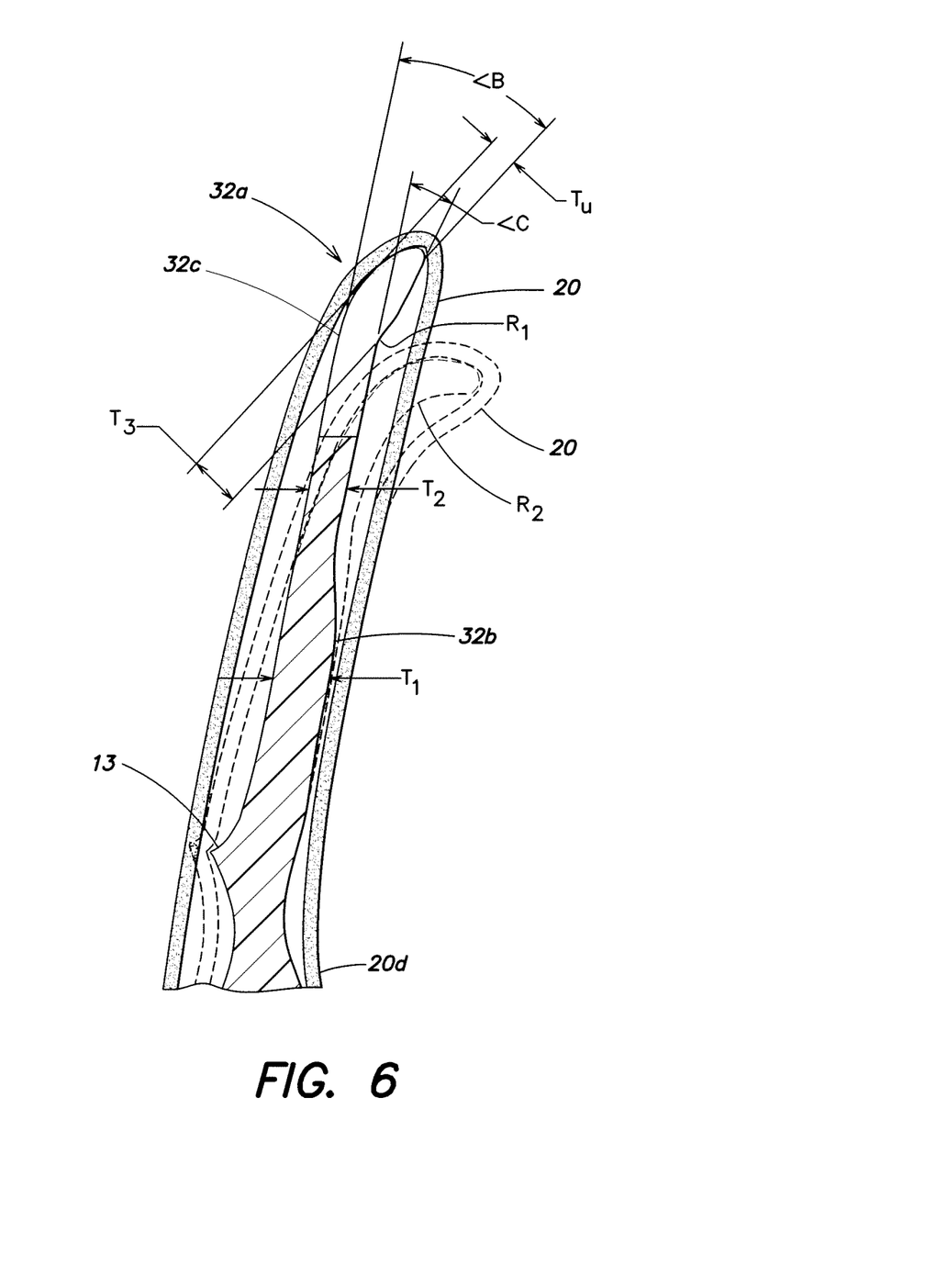
FIG. 6 is an enlarged, fragmented view of the upper haptic shown in FIG. 2.

In a further preferred embodiment, IOL 10 includes four haptics 32-35 extending from optic periphery 16. Each haptic terminates in a free end 32a-35a which extends in an anterior direction relative to the elongated section 32b-35b of the respective haptic. With reference to FIG. 6, in a preferred embodiment, haptic free ends 32a-35a extend relative to the elongated section of the respective haptic at an angle "B" of about 15° to 40° and more preferably about 33°. Each haptic free end 32a-35a may also taper from a maximum thickness $T_3$ to a minimum thickness $T_4$. The tip of each haptic free end may be beveled with a bevel angle "C" of about 10° to 20° and more preferably about 18°.

When in an unstressed state (i.e., the state when no compressive forces are being applied to the IOL), the elongated sections 32b-35b of haptics 32-35 preferably extend substantially straight although a slight curvature is possible. The free ends 32a-35a each have a length preferably about a quarter of the length of the respective elongated sections 32b-35b although this may vary. In a further preferred embodiment of the invention, the proximal haptic length (closer to periphery 16) has a thickness $T_1$ larger than the thickness $T_2$ of a respective distal haptic length (closer to the free end) (see FIG. 4). In a preferred embodiment, $T_2$ is between about 0.10 and 2.0 mm and more preferably is about 0.15 mm, and $T_1$ is between about 0.10 to 2.5 mm and more preferably about 0.2 mm. In some embodiments, the thickness decreases by at least 10%. In some embodiments, the thickness decreases by at least 15%. In some embodiments, the thickness decreases by at least 20%. Preferably, the reduction in thickness between the proximal end of the haptic and the distal end of the haptic is approximately in the range 10%-60%, and in some embodiments in the range 15%-40%, and in some embodiments in the range 20%-30%, and in some embodiments is approximately 25%.

A thickness decrease is measured excluding any portion of the length of a haptic including a PCO sharp edge 13. Additionally, the thickness decrease is measured excluding any free end, thickness features, such free end features may include a localized increase in thickness to interface with the capsular bag. For example, in some embodiments, the reduction in thickness is measured over a central portion of approximately 65% of the length of the haptics (e.g., excluding the PCO sharp edge may exclude approximately 5%-15% of the distance along the proximal portion of the haptic, and excluding the free end may exclude approximately 20% of the distal portion of the haptic). Accordingly, it is to be appreciated that, a proximal end and/or a distal end may not be the absolute ends of the haptics.

Figure 4:
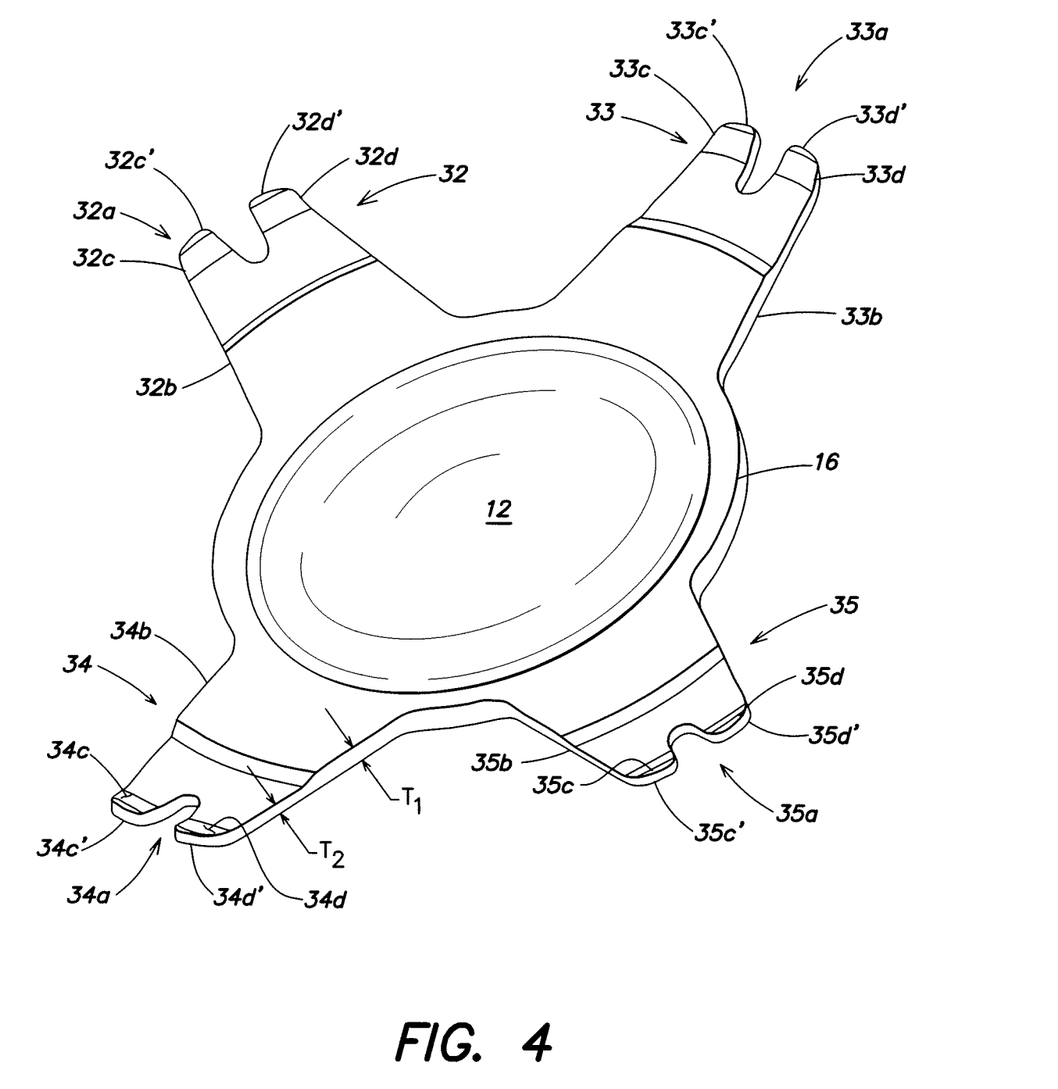
FIG. 4 is a perspective view of the IOL of FIG. 1 showing the IOL in the unstressed state.
Figure 7A:
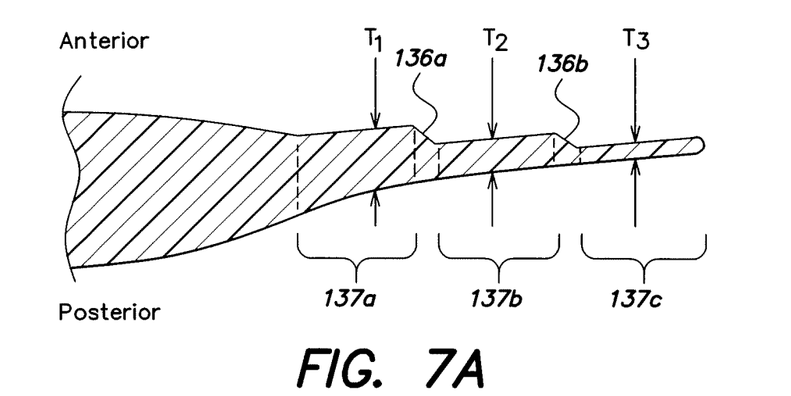
FIGS. 7A and 7B are enlarged, fragmented side views of IOL haptics having steps.
Figure 7B:
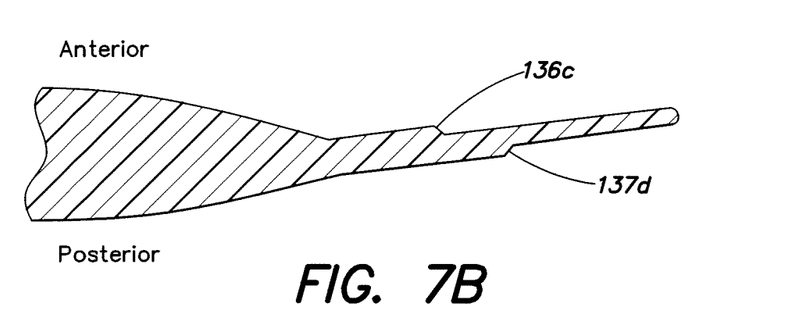

Although the embodiment of an IOL 10 illustrated in FIGS. 4 and 6 includes haptics having a single step in thickness, haptics having two, three or four or more steps may also be implemented. For example the haptic illustrated in FIG. 7A includes two steps 136a and 136b forming three regions 137a, 137b and 137c having thickness of $T_1$, $T_2$ and $T_3$, respectively. It is to be appreciated that in the illustrated embodiment each of the regions comprises a substantial portion of the length of the haptic (e.g., greater than approximately 15%, 20% or 30% of the haptic length). The regions may be equal in length. For example, in an embodiment having two steps the regions may be approximately three equal regions comprising approximately 33% of the haptic length. In an embodiment having three steps the regions may be four equal regions of approximately 25%. Although the above haptics were discussed as having regions of equal length, it is to be appreciated that some embodiments have regions of substantial but unequal lengths on a haptic. Additionally, as illustrated in FIG. 7B, in embodiments having two or more steps, at least one step 136c may be formed on an anterior surface of the haptic, and at least one step 136d formed on posterior surface of the haptic. In some embodiments the thickness is monotonically decreasing between the proximal end and the distal end. The term "monotonically decreasing" means that thickness does not increase when progressing from the proximal end to the distal end but may have one or more regions of constant thickness.

Figure 7C:
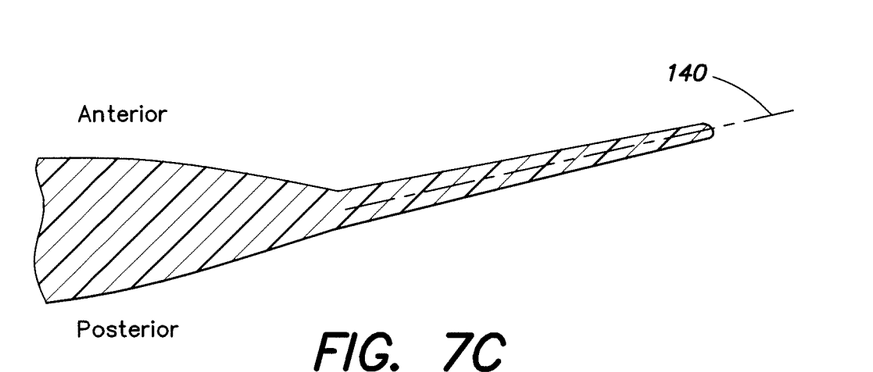
FIG. 7C is an enlarged, fragmented side view of IOL haptics having a linear reduction in thickness.

In some embodiments, the reduction in Thickness decreases smoothly (i.e., there is no step) along the entire length or along one or more of the regions. In some embodiments, as illustrated in FIG. 7C, the reduction in thickness is linear. In such embodiments, the anterior and/or posterior side of the haptic may have a slope relative to a centerline 140 that extends along the length of the haptic and through the center of the thickness of the haptic. In some embodiments having a linear reduction in thickness, the reduction when proceeding from the proximal end to the distal end is greater than 15%; and in some embodiments the reduction in thickness is greater than 25%. It is to be appreciated that aspects of the invention directed to haptics having a reduced thickness as described in any of the embodiments described above may also have an angled free end, a haptic having a concave anterior surface, and/or fingers as described herein.

Referring to FIGS. 2, 4, 5 and 6, the unstressed state of the exemplary embodiment of an IOL 10 is shown in solid lines. When implanted into the eye's capsular bag 20, the optic 11 is preferably aligned substantially along the optical axis OA with the haptics 32-35 extending radially outward therefrom. The free ends 32a-35a of the haptics are positioned toward or near the bag equator 20b. As the bag 20 begins to shrink in the weeks and months following surgery, radial compressive (stress) forces Ewe applied to the IOL 10 and particularly along the haptics 32-35 thereof. In response, the haptics 32-35 will flex with the direction of movement thereof being controlled by the free ends 32a-35a thereof.

Figure 5:
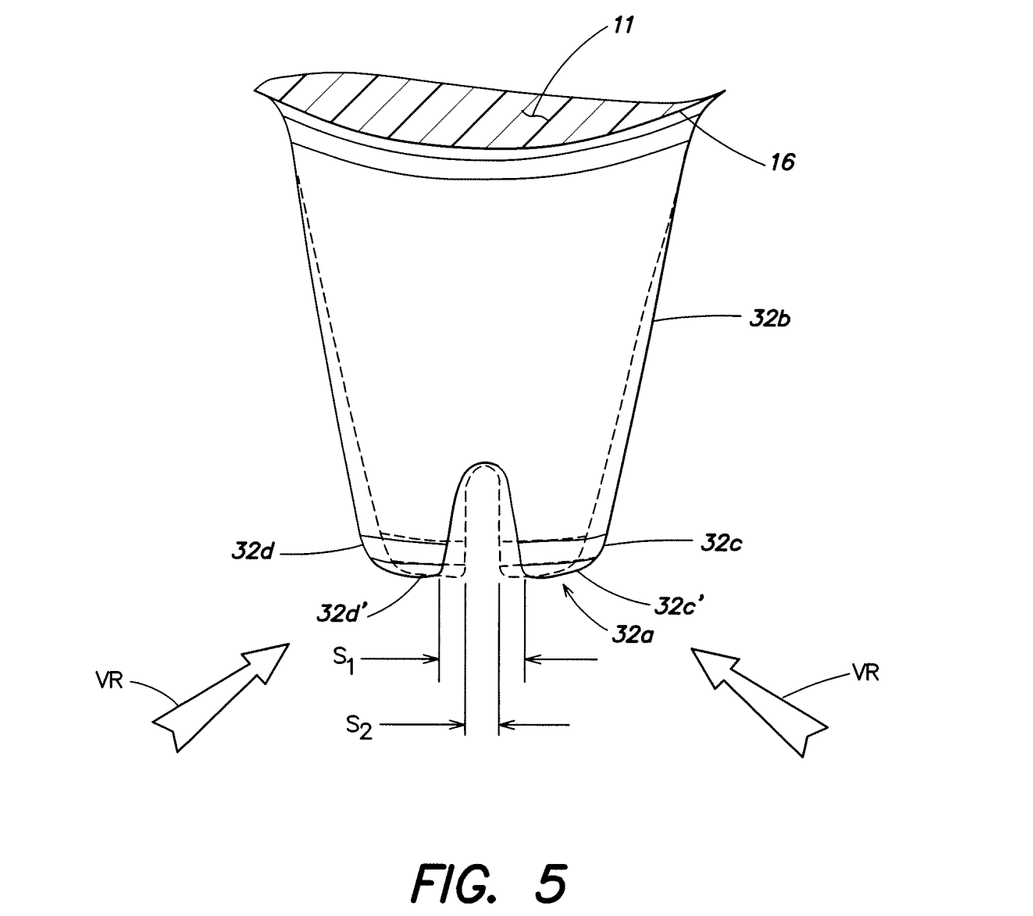
FIG. 5 is an enlarged, fragmented view of one of the IOL haptic free ends.

The stressed state of the IOL 10 is shown in dashed lines in FIGS. 2, 5 and 6. The flexing movement proceeds in this predicted manner due to the unique haptic configurations of the invention. Thus, when a compressive force is applied at the anteriorly extending free ends 32a-35a of the haptics, they respond by flexing further in an anterior direction. That is, they flex anteriorly and thereby decrease their radius of curvature from $R_1$ to $R_2$ where $R_2$ is less than $R_1$ (FIGS. 2 and 6).

In a first aspect, the haptics will flex anteriorly under a radial compressive force since the free ends 32a-35a already extend in an anterior direction (in their unstressed state as shown in solid lines) and are thus biased to continue flexing in this direction under compressive forces (to their stressed state as shown in dashed lines) as opposed to the opposite direction (i.e., posteriorly).

In a second respect, the haptics will flex anteriorly under a radial compressive force since the proximal haptic length $H_p$ (closer to periphery 16) has a thickness $T_1$ larger than the thickness $T_2$ of a respective distal haptic length $H_d$ (closer to the free end) as stated above. It is therefore practically an impossibility that the haptics would flex in the posterior direction under a radial compressive force.

It will thus be appreciated that according to aspects of the invention the anterior movement of the haptic flexing is initiated at the fee ends 32a-35a thereof. As the free ends 32a-35a flex anteriorly and thereby decrease their radius of curvature, the elongated sections 32b-35b of the haptics may also begin to flex anteriorly, predominantly at the thinner, distal haptic lengths DL thereof.

The direction of haptic flex may also be considered with regard to the relation between the plane in which the haptics flex and the plane in which optic 11 lies. More particularly, the plane in which a respective haptic may flex is indicated at $P_h$ while the optic plane is indicated at $P_o$ in FIGS. 1 and 2. It is seen in these figures that these planes extend generally perpendicular to each other. It may thus be said that the haptics will flex in a respective plane $P_h$ that extends generally perpendicular to the plane $P_o$ in which optic 11 lies.

With the haptics thus absorbing the compressive forces in the manner described above, optic 11 remains substantially aligned along the eye's optical axis OA. When so aligned, the geometric center axis GC of the optic 11 is coincident with the eye's optical axis OA as shown in FIG. 2. It is noted, however, that perfect alignment may not always be achievable due to variations in surgical techniques and capsular size, for example. Thus, while prefect alignment is the goal for best optical results, it is intended that the term "aligned" herein be interpreted to allow for less than perfect alignment between the geometric center of the optic and the eye's optical axis. It is furthermore noted that posterior movement of optic 11 is possible (along the optical axis OA), however, this is not considered a problem since firm contact between the posterior capsular wall 20a and the optic posterior surface 14 is desirable to prevent capsular opacification (PCO). In this regard, optic 11 is provided with a sharp peripheral edge 13 which together with posterior capsular wall 20a, creates a barrier to epithelial cell migration from the capsular equator to the optic 11. Epithelial cell migration is a principal cause of PCO.

Figure 8A:
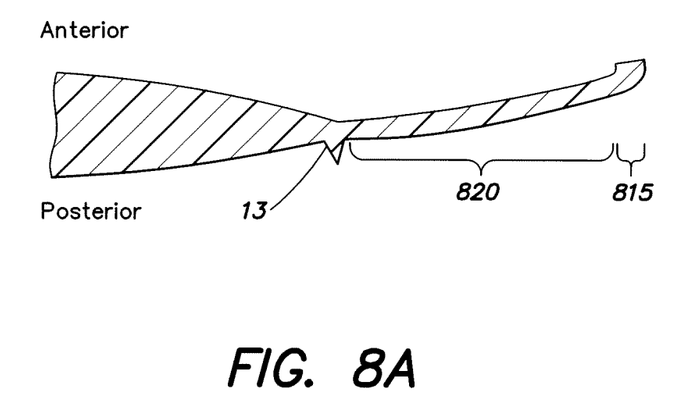
FIGS. 8A and 8B are enlarged, fragmented side views of IOL haptics having concave anterior surfaces.
Figure 8B:
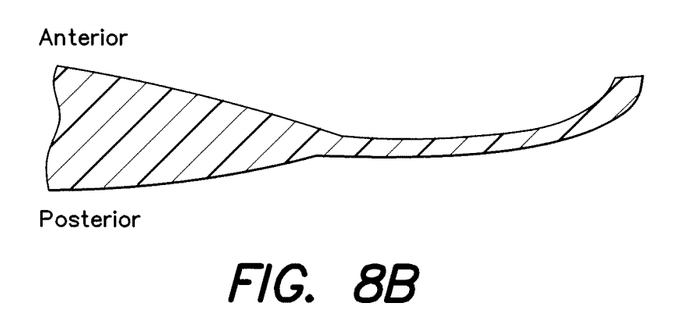

According to another aspect of the invention, the haptics may be curved along their lengths from the proximal end to the distal end, as illustrated in FIG. 8A or 813. That is, when traversing the haptic from the proximal end of the haptic to the distal end of the haptic, the lens is curved so as to be concave on the anterior surface of the haptic. In some embodiments, as illustrated in FIG. 8A, the curvature has a single curvature along the entire length of the haptic from the proximal end to the distal end. Alternatively, the haptic may comprise two or more regions along the length, each region having a different curvature (not shown). In some embodiments, as illustrated in FIG. 8B, the haptic curvature varies continuously along the length of the haptic. The curvature or curvatures along the length of a haptic may be described, for example, by one or more of polynomial curvature, such as a conic curvature (e.g., an elliptical curvature, a hyperbolic curvature or a spherical curvature), a series of planar portions approximating a curve, or a curvature described point-by-point.

In some embodiments, as illustrated in FIGS. 8A and 8B, the anterior surface and the posterior surface of the haptic have substantially the same curvatures as one another (the anterior surface being concave and the posterior surface being convex). For example, the anterior surface and the posterior surface will have substantially the same curvature if the haptic has a uniform thickness along its length or if the thickness decreases a relatively small amount along its length.

A curvature is determined excluding any portion of the length of a haptic including a PCO sharp edge 13. Additionally, the curvature of the haptic is determined excluding the free end features which may include a localized increase or decrease in curvature, for example, to interface with the capsular bag. For example, in some embodiments, the radius of curvature is measured over a central portion 820 approximately 65% of the haptics (e.g., excluding the PCO sharp edge 13 may exclude approximately 5%-15% of the distance along the haptic, and excluding free end 815 may exclude approximately 20% of the distal portion of the haptic). It is to be appreciated that embodiments including a curvature as described above predispose a lens to move posteriorly upon radial compression resulting from shrinking of the capsular bag, and operates to maintain centration of the lens in a capsular bag. It is to be appreciated that aspects of the invention directed to a haptics having a curvature as described above may also have an angled free end, a reduced thickness, and/or fingers as described herein.

In a further aspect of the invention, the haptic free ends 32a-35a each comprise at least two spaced fingers 32c,d-35c,d, respectively (FIGS. 1, 4 and 5). In some embodiments each finger pair extends substantially parallel to each other with the extreme tips 32c',d-35c',d' thereof lying in a plane which is generally perpendicular to the geometric center axis GC of optic 11. As compressive forces are applied to the fingers, the two fingers of a respective haptic may move toward one another to reduce or close the space therebetween such as from space $S_1$ to a space $S_2$ as shown in FIG. 5. This movement absorbs particularly those compressive forces having a vector component directed tangentially to the circumference of the lens such as represented by vectors $V_R$, for example, that are created by the dynamics of the shrinking capsular bag. In particular, the fingers are deformable toward one another in a tangential direction. It is to be appreciated the tangential force addressed by the fingers is perpendicular to the radial force addressed by the angle and curvature of the haptics discussed above. This aspect of the invention is particularly advantageous when combined with a thin lens design in that it also helps maintain the structural stability of the lens. This aspect is also advantageous when combined a structure capable of adapting to radial compressive forces such as a haptic having an anteriorly curved surface, a haptic that decreases in thickness from the proximal end to the distal end and/or haptics having angled free ends as described above. It is to be appreciated that, when used in such a combination, the lens is capable of maintaining stability in the presence of both tangential and radial forces which may result from capsular bag shrinkage.

Figure 9A:
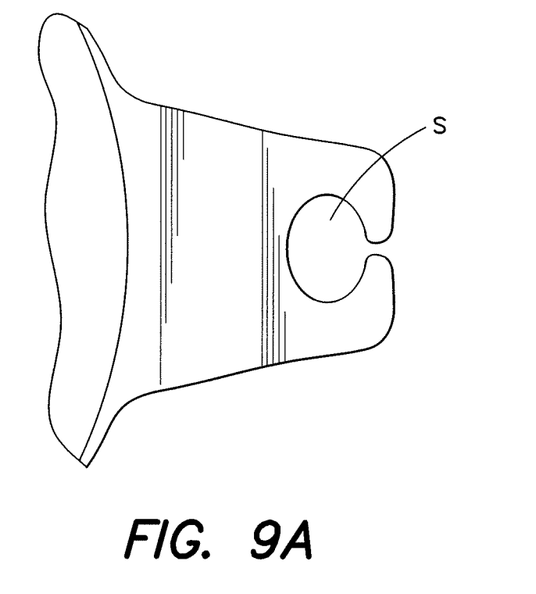
FIGS. 9A and 9B are enlarged, fragmented top views of IOL haptics having fingers.
Figure 9B:
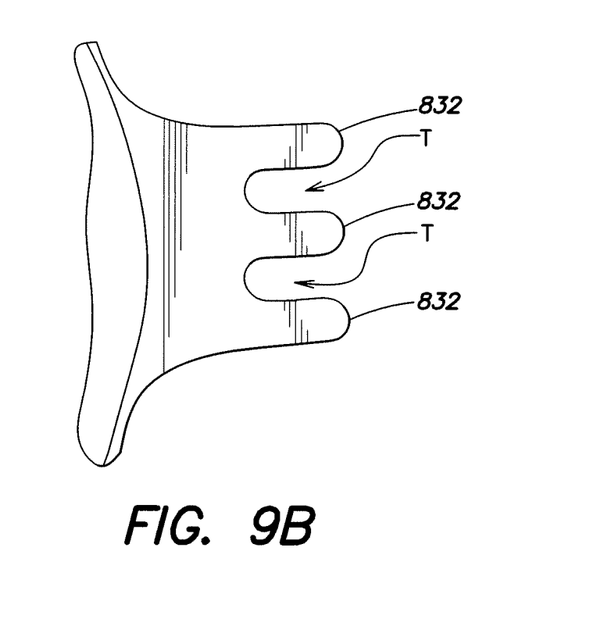

Although the embodiment of an IOL illustrated in FIG. 1 has U-shaped notch N, the groove may have any suitable shape. For example, the IOL illustrated in FIG. 9A includes a bulb-shaped notch S. Also, although the exemplary embodiment of an IOL illustrated in FIG. 1 has two fingers, IOLs may have three, four, five or more fingers. For example, the IOL illustrated in FIG. 9B includes three fingers 832 and two notches T.

In a further preferred embodiment, the tips of the fingers 32c,d-35c,d extend at an angle of between about 10° and 50° relative to the remainder of the free end, and more preferably extends at an angle of between about 20° and 40°, and most preferably extends at an angle of about 33° relative to the remainder of a respective free end. It will be noticed that the angle corner may be located approximately mid-way along the space $S_1$ between each finger pair although this may vary.

It will thus be appreciated that haptics according to aspects of the invention are capable of absorbing compressive forces having a multitude of vectors such as those created by the dynamics of a shrinking capsular bag while the IOL optic 11 remains substantially aligned along the eye's optical axis as intended.

What is claimed:

1. A foldable IOL for placement in an evacuated capsular bag of an eye, said IOL comprising:
    a) an optic having opposite anterior and posterior surfaces defining a geometric center and a periphery, the posterior surface of the optic having a sharp barrier edge for the prevention of PCO;
    b) at least two haptics extending from said periphery, each of said haptics having an elongated section and terminating in a free end that is angled in an anterior direction with respect to said elongated section;
    whereby when implanted in the evacuated capsular bag of an eye with said geometric axis generally aligned along the optical axis of the eye, the free ends of said haptics will each flex in a respective plane that extends generally perpendicular to the plane in which optic lies in response to a radial compressive force applied thereto while said optic geometric center axis remains generally aligned with said optical axis.

2. The IOL of claim 1 wherein said elongated section of each said haptic extends substantially straight when in an unstressed condition.

3. The IOL of claim 2 wherein said free end of each haptic extends at an angle of between about 10° and 50° relative to said elongated section of a respective free end.

4. The IOL of claim 2 wherein said free end of each haptic extends at an angle of between about 20° and 40° relative to said elongated section of a respective free end.

5. The IOL of claim 2 wherein said free end of each haptic extends at an angle of about 33° relative to said elongated section of a respective free end.

6. The IOL of claim 2 wherein each said haptic has a distal length adjacent said free end thereof and a proximal length adjacent said optic periphery, and wherein said distal length is thinner than said proximal length.

7. The IOL of claim 1 wherein each free end comprises at least two spaced fingers lying in a common plane which extends generally perpendicular to the axis of said optic geometric center, said at least two spaced fingers being movable toward one another in response to a compressive force applied thereto.

8. The IOL of claim 7 wherein each of said free ends include a beveled tip.

9. The IOL of claim 8 wherein said beveled tip has a bevel angle of about 10° to 20°.

10. The IOL of claim 8 wherein said beveled tip has a bevel angle of about 18°.

11. The IOL of claim 1 wherein said haptics each have a maximum thickness of about 0.2 mm.

12. The IOL of claim 1 wherein said lens is made from acrylic.

13. The IOL of claim 1 wherein each of said free ends include a beveled tip.

14. The IOL of claim 13 wherein said beveled tip has a bevel angle of about 10° to 20°.

15. The IOL of claim 13 wherein said beveled tip has a bevel angle of about 18°.

16. A foldable IOL comprising:
    a) an optic having opposite anterior and posterior surfaces having a geometric center axis and a periphery the posterior surface of the optic having a sharp barrier edge for the prevention of PCO;
    b) at least two haptics extending from said periphery, each of said haptics having an elongated section and terminating in a free end that is angled in an anterior direction with respect to said elongated section, each of said free ends comprising at least two fingers, the fingers being spaced apart from one another.

17. The IOL of claim 16 wherein the free ends extend in an anterior direction relative to a respective elongated section.

18. The IOL of claim 16 wherein for each of the free ends the at least two fingers extend substantially parallel to each other, and wherein each finger on all of the free ends comprises a tip and all of the tips lie in a plane which is generally perpendicular to the geometric center axis of said optic.

19. The IOL of claim 17 wherein each said free end extends at an angle of between about 10° and 50° relative to said elongated section of said free end.

20. The IOL of claim 17 wherein said free end of each haptic extends at an angle of between about 20° and 40° relative to said elongated section of a respective free end.

21. The IOL of claim 17 wherein said free end of each haptic extends at an angle of about 33° with respect to said elongated section of a respective free end.

22. The IOL of claim 17 wherein said free end of each haptic comprises about 25% of the length of a respective elongated section.

23. The IOL of claim 17 wherein said lens is flexibly movable between a first, unstressed configuration and a second, stressed configuration.

24. The IOL of claim 23 wherein when said lens is in said unstressed configuration, said elongated sections of said haptics are substantially straight and when in said stressed configuration, at least part of said elongated sections are curved.

25. The IOL of claim 23 wherein when in said stressed configuration, said free ends decrease their radius of curvature in the anterior direction.

26. The IOL of claim 1, wherein the elongated section of each haptic vaults anteriorly relative to the plane of the optic.

27. The IOL of claim 1, wherein the elongated section of each haptic vaults anteriorly relative to the plane of the optic at an angle of between 5 and 15 degrees.

28. The IOL of claim 16, wherein the elongated section of each haptic vaults anteriorly relative to the plane of the optic.

29. The IOL of claim 16, wherein the elongated section of each haptic vaults anteriorly relative to the plane of the optic at an angle of between 5 and 15 degrees.

* * * * *